United States Patent [19]

Howell et al.

[11] Patent Number: 5,268,173

[45] Date of Patent: Dec. 7, 1993

[54] SUPPRESSION OF GLIOCLADIUM VIRENS PHYTOTOXIN PRODUCTION WITH STEROID INHIBITORS

[75] Inventors: Charles R. Howell; Robert D. Stipanovic, both of Bryan, Tex.

[73] Assignee: The United States of America as represented by the United States Secretary of Agriculture, Washington, D.C.

[21] Appl. No.: 901,439

[22] Filed: Jun. 19, 1992

[51] Int. Cl.$^5$ .................. C12N 1/14; A01N 63/00
[52] U.S. Cl. ..................... 424/93 Q; 435/254.1; 435/911
[58] Field of Search .................. 424/93 R, 93 Q; 435/254, 911

[56] References Cited

U.S. PATENT DOCUMENTS

| | | | |
|---|---|---|---|
| 3,952,002 | 4/1976 | Kramer et al. | 260/308 |
| 4,079,062 | 3/1978 | Van Reet et al. | 260/308 |
| 4,510,136 | 4/1985 | Moberg | 514/63 |

OTHER PUBLICATIONS

Howell, C. R. et al. Can. J. Microbiol. 29(3), pp. 321-324, 1983.

Howell, Charles R., "Biological Control of Pythium Damping-Off by Coating Cottonseed with Gliocladium Viren Preparations", Beltwide Cotton Production Research Conferences, Jan. 9-14, 1990, Las Vegas, Nevada, p. 31.

Howell, C. R., "Biological Control of Pythium Damping-Off of Cotton With Seed-Coating Preparations of Gliocladium Virens", Phytophathology, An International Journal. vol. 81, No. 7, Jul. 1991, pp. 738-741.

Howell, C. R. et al., "Phytotoxicity to Crop Plants and Herbicidal Effects on Weeds of Viridiol Produced by Gliocladium virens", vol. 74, No. 11, 1984, pp. 1346-1349, Phytopathology.

Jones, Richard W., et al., "Plant Growth Response to the Phytotoxin Viridiol Produced by the Fungus Gliocladium virens", Weed Science, Issue 5, (Sep.) 1988, vol. 36:683-687.

Jones, Richard W., et al., "Conversion to Viridin to Viridiol by Viridin-producing Fungi", Can. J. Microbiol., vol. 33, 1987, pp. 963-966.

Howell, C. R., et al., "Antibiotic Production by Gliocladium virens and Its Relation to the Biocontrol of Seedling Diseases", Petria, Giornale di Patologia delle Piante, vol. 1(2), maggio 1991, 79-156, pp. 129-130.

Howell, Charles R., "Problems and Progress in Development of Fungi as Biological Control Agents of Plant Diseases", Abstracts, 8th NACOM Innovation & Hierarchical Integration, Jackson, Wyoming, Sep. 5-8, 1990, p. 144.

Howell, C. R., et al., "Antibiotic Production by Gliocladium Virens and Its Relation to the Biocontrol of Cotton Seedling Diseases", 1991 Proceedings Beltwide Cotton Conference, p. 183.

Howell, C. R., "Biological Control of Cotton Seedling Damping-Off By Coating Cottonseed With Gliocladium Virens Preparations", Phytopathology, An International Journal, vol. 80, No. 10, Oct. 1990.

*Primary Examiner*—Douglas W. Robinson
*Assistant Examiner*—Kristin Larson
*Attorney, Agent, or Firm*—M. Howard Silverstein; Randall E. Deck; John D. Fado

[57] ABSTRACT

A process for producing cultures of *Gliocladium virens* for use as biocontrol agents wherein the production of viridiol is inhibited. Cells of *Gliocladium virens* are grown in a culture medium and under conditions effective to produce gliotoxin and/or gliovirin, wherein the culture medium includes an amount of a fungicidal steroid inhibitor which is effective to inhibit production of viridiol but which does not substantially inhibit the growth of *G. virens*. Following recovery, the resultant culture may be used as a biocontrol agent for the control of plant diseases by application to the locus of a plant, seedling or seed to be protected. Coating seeds with the biocontrol agent prior to planting has been found to be particularly effective for the control of soilborne root or seedling diseases.

29 Claims, No Drawings

SUPPRESSION OF GLIOCLADIUM VIRENS PHYTOTOXIN PRODUCTION WITH STEROID INHIBITORS

BACKGROUND OF THE INVENTION

1. Field of the Invention

The invention relates to a biological control agent for control of fungal diseases in plants.

2. Description of the Prior Art

*Gliocladium virens* has been recognized as a mycoparasite and antibiotic-producing antagonist of plant pathogens, and has been used as an effective biocontrol agent of several soilborne root or seedling diseases [Aluko and Hering, 1970, Trans. Br. Mycol. Soc., 55:173-179; Beagle-Ristaino and Papavizas, 1985, Phytopathology, 75:560-564; Howell, 1982, Phytopathology, 72:496-498; Howell and Stipanovic, 1983, Can. J. Microbiol., 29:321-324; Weindling and Fawcett, 1936, Hilgardia, 10:1-16; and Wright, 1956, Plant Soil, 8:132-140]. *G. virens* produces gliotoxin and gliovirin, which are particularly effective antifungal antibiotics, as well as the antibacterial compound heptelidic acid and the antifungal compound viridin.

In addition to its use as an antifungal biocontrol agent, *G. virens* has also been employed as a mycoherbicide [Jones et al., 1988, Weed Science, 36:683-687; and Howell and Stipanovic, 1984, Phytopathology, 74:1346-1349]. Herbicidal activity has been attributed to the production of viridiol, a steroidal phytotoxin.

Unfortunately, viridiol has not only been shown to be phytotoxic to weeds such as pigweed, but also to valuable crop plants such as cotton seedlings [Howell et al., Phytopathology, 74:1346-1349 (1984)]. Thus, the production of the phytotoxic compound viridiol may severely restrict the use of *G. virens* as a biocontrol agent for the control of plant diseases, limiting the amount of *G. virens* that can be applied to crops.

SUMMARY OF THE INVENTION

We have now discovered a process for producing cultures of *Gliocladium virens* for use as biocontrol agents wherein the production of viridiol is inhibited. Cells of *Gliocladium virens* are grown in a culture medium and under conditions effective to produce gliotoxin and/or gliovirin. We have unexpectedly found that a fungicidal steroid inhibitor may be added to the culture medium in an amount which is effective to inhibit production of viridiol but which does not substantially inhibit the growth of *G. virens*. Following recovery, the resultant culture may be used as a biocontrol agent for the control of plant diseases by application to the locus of a plant, seedling or seed to be protected. Coating seeds with the biocontrol agent prior to planting has been found to be particularly effective for the control of soilborne root or seedling diseases.

In accordance with this discovery, it is an object of this invention to provide a biocontrol agent for the control of plant diseases which is not phytotoxic to the plant being treated.

It is also an object of this invention to provide an improved process for producing cultures of *G. virens* for use as biocontrol agents having substantially reduced levels of viridiol.

Other objects and advantages of this invention will become readily apparent from the ensuing description.

DETAILED DESCRIPTION OF THE INVENTION

The fungal organism for use in this invention is *Gliocladium virens*. Traditionally, strains of this organism have been separated into one of two broad groups, designated P and Q, based upon viridin and pigment production. We have found that these groups differ not only in colony pigmentation, but also in antibiotic production, with the P group producing yellow pigment and gliovirin but not gliotoxin, and the Q group producing gliotoxin but not gliovirin or the pigment [Howell and Stipanovic, 1991, Petria, 1:129-130, the contents of which are incorporated by reference herein]. Owing to differences in activity of these antibiotics, strains from either group may be selected in accordance with their efficacy against a given target disease. For example, when activity against the causative agent of root rot of white beans, i.e. *Rhizoctonia solani*, is required, Q strains are preferred. In contrast, P strains are preferred when the target pathogen is *Pythium ultimum*, the causative agent of cotton seedling disease (damping-off). When a broad spectrum of activity is desired, mixtures of one or more strains from each group may be used, enabling production of both gliotoxin and gliovirin.

The fungi may be cultivated by any conventional means under any conventional aerobic conditions that promote their growth. Under cultivation conditions the subject fungi will produce gliotoxin and/or gliovirin concurrently with growth, and the fermentation should be continued for sufficient time to produce maximum levels of cells and antibiotics, ideally about 4 to 6 days. Effective conditions for the fermentation, including pH, temperature and time, may be readily determined by the practitioner in the art. A variety of culture media are also suitable for use in the invention. The culture media that are optimal for growth and production of gliovirin and gliotoxin will vary with the strain of *G. virens* used, and may be readily determined using conventional techniques. Without being limited thereto, suitable media are described by Howell [Phytopathology, 1991, 81:738-741, the contents of which are incorporated by reference herein] and include wheat, wheat bran, sorghum, soybean, cotton, rice, oats, or supplemented peat moss. However, millet or rice hull media are particularly preferred, with a plurality of strains of *G. virens* exhibiting greater biocontrol activity when grown thereon.

To inhibit the production of viridiol, a fungicidal steroid biosynthesis inhibitor is added to the culture medium prior to or during the fermentation. Steroid inhibitors are generally recognized as fungicidal, and a number of steroid inhibitors have been employed commercially as fungicides as described, for example, by Polak [Mode of Action Studies, In: Ryley ed. Chemotherapy of Fungal Diseases, Springer-Verlag, Berlin, 1990, pages 153-179] and Thomson [Agricultural Chemicals, Book IV-Fungicides, Thomson Pub., Fresno, Calif., 1991]. However, we have unexpectedly discovered that viridiol production can be inhibited or blocked without substantially inhibiting *G. virens* growth and antibiotic production by adding low concentrations of these steroid biosynthesis inhibitors.

It is anticipated that a variety of steroid production inhibitors or mixtures thereof may be used. Without being limited thereto, inhibitors belonging to the classes of triazole and silane steroid inhibitors are preferred, with propiconazole, flusilazole, myclobutanil and triadimenol, and to a lesser extent bitertanol, penconazole, and triadimefon, being particularly preferred. The efficacy of a given inhibitor will vary to some extent with the strain of *G. virens* on which it is used. For example, propiconazole is more effective with strains belonging to the P group than the Q group, while flusilazole, myclobutanil and triadimenol are more effective with Q group strains. The selection of other suitable steroid inhibitors may be readily determined by the practitioner skilled in the art.

The steroid inhibitor should be added to the culture in an amount which is effective to inhibit production of viridiol but which does not substantially inhibit the growth of the *G. virens*, in comparison with an untreated culture of the same strain(s) of *G. virens*. A "substantial" inhibition of growth is defined herein as reducing the growth of *G. virens* by more than about 25% relative to an untreated control culture. Effective concentrations will vary with both the particular strain of *G. virens* and the inhibitor used, and may be readily determined by the skilled practitioner using techniques conventional in the art. Generally, concentrations of inhibitor in the culture medium between about 0.5 and about 1 ppm are preferred. However, the practitioner will recognize that concentrations less than 0.5 ppm or greater than 1 ppm may also be effective.

Following completion of the the fermentation, the resultant culture of *G. virens* containing gliovirin and/or gliotoxin may be recovered or harvested for use as a biocontrol agent. As a practical matter, it is envisioned that commercial formulations of the subject biocontrol agent would be prepared directly from the culture, thereby obviating the need for any purification steps. While the aqueous cultures could be applied while still in liquid phase, in the preferred embodiment, the water is removed from liquid cultures to partial or substantial dryness, and the dried culture broken up or ground into small particles using techniques conventional in the art. Without being limited thereto, suitable water removal techniques include air drying, evaporation or filtration.

In a particularly preferred embodiment, the granules are contacted with a sticking agent or adherent as are known in the art to facilitate adherence of the biocontrol agent to a target seedling or seed to be treated. Suitable sticking agents may be readily determined by the skilled practitioner and include but are not limited to latex (RHOPLEX B-15, Rohm and Haas, Philadelphia, Pa.), sugars such as sucrose, glucose, fructose, mannose, α-methyl glucoside or corn syrup (as described by Shasha and McGuire, U.S. Pat. No. 5,061,697, issued Oct. 29, 1991, the contents of which are incorporated by reference herein), alginate, methylcellulose, and OPADRY (Colorcon, Inc., Westpoint, Pa.). The sticking agent may be applied onto either the granules or seed prior to use. When seeds are being treated, they may be precoated with biocontrol agent prior to sale by the seed supplier, or they may be coated in the field.

In an alternative embodiment, controlled release of the biocontrol agent may be accomplished by encapsulation within an inert carrier using conventional techniques. Suitable carriers of this type include but are not limited to alginate gels, wheat-gluten matrices, starch matrices, or synthetic polymers as are known in the art. Preferred alternative carriers and methods for immobilizing nematodes are described, for example, in Walker et al. or Connick (U.S. Pat. Nos. 4,767,441 and 4,401,456, respectively, disclosing alginate gels), Connick and Nickle (U.S. patent application Ser. No. 07/560,792, filed Jul. 30, 1990, disclosing wheat gluten), Doane et al. (U.S. Pat. No. 4,911,952 disclosing starch matrices), and Trimnell et al. (U.S. Pat. No. 4,439,488 disclosing polyhydroxy polymer borates), the contents of each of which are herein incorporated by reference.

Besides the culture, other additives and adjuncts may be formulated into the subject biocontrol composition. Examples of these include additional nutrients, inert fillers, UV protectants such as Congo-red, folic acid, paraminobenzoic acid or azobenzene, fertilizers, or pesticides. Particularly preferred for inclusion are additional fungicides other than those described hereinabove. Without being limited thereto, suitable fungicides include carboxin, pentachloronitrobenzene or metalaxyl, which are commonly used as cottonseed treatments to control seedling diseases. Unexpectedly, when reduced concentrations of metalaxyl were used in combination with the biocontrol agent as a seed coating, a synergistic effect was observed. It is also understood that additional steroid inhibitor may be added to the culture following completion of the fermentation, to ensure that the agent retains an effective amount of inhibitor to inhibit viridiol production after it is applied.

To be effective, the biocontrol agent must be applied to the locus of, or in the vicinity of, the plant, seedling or seed to be protected. In one preferred embodiment, the biocontrol agent is applied as a seed treatment coated onto the seeds, thus assuring the presence and production of antibiotics in the vicinity of the growing plant. In another preferred embodiment, the biocontrol agent may be applied into the furrows together with the seed during planting. Ideally, particulate biocontrol agent (with or without sticking agent) will be admixed with the seeds in the planter hopper to ensure its application into the furrow in close proximity to the seed. The practitioner skilled in the art will recognize that while the biocontrol agent could be separately applied to the soil or, in the case of greenhouse plants, added to potting mix of plants grown in greenhouse conditions [Lumsden et al., 1990, Phytopathology, 79:361–366; and Smith et al, 1990, Phytopathology, 80:880–885], such techniques require relatively large volumes of the biocontrol agent which are impractical in the field.

Depending upon the species of the target disease, the subject biocontrol agent acts to control the causative fungal pathogen by death inducement or inhibiting growth or infectivity, all of which mechanisms are evidenced by a decrease in the incidence or severity of the plant or seedling disease associated with the pathogen. The biocontrol agent of this invention is administered in an amount effective to control a target disease as determined by routine testing. An "effective amount" of biocontrol agent is defined herein as those quantities of agent that will result in a significant decrease in the incidence or severity of the plant or seedling disease as compared to an untreated control. The actual effective amount will vary with the disease and causative fungal pathogen, the strain of *G. virens*, the steroid inhibitor, the formulation and method of treatment, and environmental conditions, and may be readily determined by the practitioner skilled in the art. When applied as a coating on cotton seeds, suitable amounts of biocontrol agent range from, but are not limited to, greater than about 0.5–1 g of dried particulate biocontrol agent per 100 cottonseeds.

The biocontrol agent encompassed herein is effective in controlling plant and seedling diseases of a plurality of plants. Without being limited thereto, the agent may be applied to any agronomically important plant or its seedling or seed, especially seeds of cotton, soybeans, beans, citrus, apples and zinnia.

In an alternative embodiment for the production of the biocontrol agent, steroid inhibitor may be combined with cells of *G. virens* after, rather than prior to or during, the fermentation. Because this embodiment would inhibit the production of viridiol only after application of the agent to the locus of the plant or soil, significant levels of viridiol produced during the fermentation would still be present. Although this residual viridiol may be reduced from the fermentation medium by separation techniques such as filtration, both the cost of such a separation and the attendant loss of antibiotics would be substantial.

The following examples are intended only to further illustrate the invention and are not intended to limit the scope of the invention which is defined by the claims.

EXAMPLE 1

Preparation and Culture of *G. virens*. Ehrlenmeyer flasks (250 ml) containing 5 g of ground millet ($\leq 1$ mm particle size) and 95 ml of $H_2O$ were autoclaved twice on subsequent days. Sterol inhibitors dissolved in acetone were then added to the flasks in 1 ml aliquants to make 0.5 or 1 ppm final concentrations in the medium. Controls received 1 ml aliquants of acetone. Potato Dextrose Agar Plugs (0.5 mm) from actively growing and sporulating agar cultures of six different strains of *G. virens* (3 P group strains and 3 Q group strains) were transferred to the liquid cultures, and the cultures were shake incubated at 25° C. for 6 days. Each treatment consisted of six replicated cultures.

Harvest and Extraction Procedures. The culture contents of the first three replications were centrifuged at 16,000 X G for 10 min, and the supernatant fluids were separated from the pellets. Each pellet was extracted with 75 ml of 80% acetone, the solids removed by centrifugation, and the acetone was removed in vacuo. The aqueous residue remaining was combined with the original supernate, and the entire mixture was extracted with 100 ml of chloroform. The chloroform was removed in vacuo and the residue was dissolved in 2 ml of methanol. The culture contents of replications 3 through 6 were also centrifuged and the supernatant fluids were discarded. The pellets were spread on sterile petri dishes and the contents were allowed to air dry for two days. The air dry preparations were then ground in a Wiley mill and sieved to obtain particle sizes $\leq 500$ $\mu$m.

HPLC Fractionation of Culture Extracts. Compounds in the chloroform extracts were separated, using a Hewlett Packard 1090 liquid chromatograph equipped with a diode array detector. The effluent was monitored at 254 nm, and the column (Scientific Glass Engineering C-18, 250X4.6 mm, 5 $\mu$m packing) was heated to 40° C. The mobile phase (1.25 ml/min) consisted of water (0.07% $H_3PO_4$) and acetonitrile (ACN). Development of the chromatogram was isocratic (80% acid: 20% ACN) for 5 min, followed by a linear gradient to 72% acid: 28% ACN over one min, and held at this ratio for an additional 12 min. The instrument was calibrated by injecting known quantities of authentic samples of gliotoxin, gliovirin, viridin, and viridiol.

As shown in Table 1, treatment of the *G. virens*/millet cultures with sterol biosynthesis inhibitors almost completely suppressed the production of the steroids viridin and viridiol, while synthesis of the non-steroid antibiotics, gliotoxin and gliovirin, was not suppressed. However, the efficacy of a given inhibitor was dependent on the strain of *G. virens* on which it was used (Table 2). In general, Propiconazole (1-(2-(2,4-dichlorophenyl)-4-propyl-1,3-dioxolan-2-ylmethyl)-1H-1,2,4-triazole) was more effective with strains belonging to the P group (gliovirin producers) than with strains of the Q group (gliotoxin producers). The others, Triadimenol (Beta(4-chlorophenoxyl)-alpha-(1,1-dimethylethyl)-1H-1,2,4-triazole-1-ethanol), Myclobutanil (alpha-butyl-alpha(4-chlorophenyl)-1H-1,2,4-triazole-1-propenenitride), and Flusilazole (bis-(4-nuorophenyl) methyl (1H-1,2,4-triazole-1-ylmethyl)silane) were more effective with Q group strains.

Phytotoxicity and Disease Assay. Cottonseeds treated with *G. virens*/millet preparations, at a dose of 0.05-g/seed, with and without sterol inhibitor added, were planted in 5-g each of unsterile cotton field soil (Lufkin fine sandy loam). The soil was contained in 18- X 50-mm test tubes. Soil moisture was 20% by weight and one seed was planted in each tube. The tubes were incubated for 6 days at 25° C. and a 12-h photoperiod; the contents were then washed from the tubes and examined. Each treatment consisted of 10 replicate tubes arranged in a completely randomized design. The same procedure was carried out in soil infested with Pythium ultimum at the rate of 2,000 oospores/g of soil, except that the treatments were coated onto the seed with a latex sticker and the tubes were incubated in the dark at 18° C. for one wk before transfer to 25° C. and a 12-h photoperiod.

The radicles of cottonseed treated with *G. virens* preparations to which sterol inhibitor had not been added were stunted, and the apical meristems were necrotic. Cottonseed treated with *G. virens* preparations containing sterol inhibiting produced healthy and normal radicles. Cottonseed planted in *Pythium ultimum* infested soil and treated with *G. virens* (P strain) preparations, with sterol inhibitor added, produced only 20% damped-off seedlings, whereas 70% of the nontreated control were damped off.

EXAMPLE 2

Effect of Altered Culture Conditions. Cultures of 5% millet were treated with sterol inhibitor, inoculated with *G. virens*, harvested, extracted, and fractionated as described above, except that 1% ground peat moss was added to the cultures and the pH was adjusted to 4.0 prior to inoculation.

Treatment with sterol inhibitor of *G. virens* (Q strains)/millet cultures with peat moss added and adjusted to pH 4.0 with HCl did not suppress viridiol production by the fungus. Control cultures of strains G-6 and G-11 produced 2560 and 2580 $\mu$g/ml of viridiol, respectively, while cultures of these same strains treated with 1 ppm of flusilazole produced 2630 and 2823 $\mu$g/ml of viridiol.

TABLE 1

Effect of sterol inhibitors on the production of the phytotoxin viridiol and other secondary metabolites by *Gliocladium virens* in culture

| Strain/inhibitor | Phytotoxin and Antibiotics ($\mu$g/ml) | | | |
|---|---|---|---|---|
| | Viridiol | Viridin | Gliotoxin | Gliovirin |
| P strains | | | | |
| G-4 + NT | 1510 | 110 | — | 2683 |
| G-8 + NT | 1253 | 70 | — | 1683 |
| G-9 + NT | 1990 | 40 | — | 2210 |
| G-4 + PC | — | 40 | — | 2563 |

TABLE 1-continued

Effect of sterol inhibitors on the production of the phytotoxin viridiol and other secondary metabolites by *Gliocladium virens* in culture

| Strain/inhibitor | Phytotoxin and Antibiotics (μg/ml) | | | |
|---|---|---|---|---|
| | Viridiol | Viridin | Gliotoxin | Gliovirin |
| G-8 + PC | — | 55 | — | 2823 |
| G-9 + PC | 40 | 140 | — | 860 |
| Q strains | | | | |
| G-6 + NT | 2410 | 30 | 770 | — |
| G-11 + NT | 3100 | 40 | 980 | — |
| G-20 + NT | 2430 | 70 | 1180 | — |
| G-6 + FL | — | — | 633 | — |
| G-11 + FL | — | — | 730 | — |
| G-20 + FL | — | — | 803 | — |

NT = Nontreated Control; PC = Propiconazole (0.5 ppm); FL = Flusilazole (1 ppm)

TABLE 2

Viridiol production by P and Q strains of *Gliocladium virens* in the presence of sterol inhibitors.

| Strain | Sterol Inhibitors | | | | | | |
|---|---|---|---|---|---|---|---|
| | BL | FL | ML | PC | PE | TL | Tn |
| P strains | Viridiol Production (μg/ml) | | | | | | |
| G-4 | 1020 | 1890 | 1100 | — | 350 | 1560 | 2180 |
| G-8 | 80 | — | 110 | — | — | 40 | 810 |
| G-9 | 1940 | 860 | 50 | — | 450 | 800 | 1060 |
| Q strains | | | | | | | |
| G-6 | — | — | — | 1410 | — | — | 1640 |
| G-10 | — | — | — | — | — | — | trace |
| G-11 | 70 | — | — | 1610 | — | — | 1480 |

BL = Bitertanol; FL = Flusilazole; ML = Myclobutanil; PC = Propiconazole; PE = Penconazole; TL = Triadimenol; TN = Triadimefon Concentration of PC = 0.5 ppm; the remainder = 1 ppm.

We claim:

1. A process for producing a *Gliocladium virens* culture useful as an anti-fungal agent comprising:
   (a) culturing cells of *Gliocladium virens* in a culture medium and under conditions effective to produce gliotoxin or gliovirin, and wherein said culture medium includes an amount of a fungicidal steroid inhibitor effective for inhibiting production of viridiol by said Gliocladium, without substantially inhibiting growth of said Gliocladium, and
   (b) recovering the culture resulting from step (a).

2. The process as described in claim 1 wherein said steroid inhibitor is selected from the group consisting of triazoles, silanes and mixtures thereof.

3. The process as described in claim 2 wherein said steroid inhibitor is selected from the group consisting of propiconazole, flusilazole, triadimenol, myclobutanil and mixtures thereof.

4. The process as described in claim 1 wherein the amount of said steroid inhibitor is between about 0.5 to about 1 ppm.

5. The process as described in claim 1 further comprising the step of removing water from said culture.

6. The process as described in claim 1 further comprising the step of encapsulating said culture.

7. A composition for use as a anti-fungal agent comprising the culture produced by the process of claim 1.

8. A composition for use as a anti-fungal agent comprising the culture produced by the process of claim 2.

9. A composition for use as a anti-fungal agent comprising the culture produced by the process of claim 3.

10. A composition for use as a anti-fungal agent comprising the culture produced by the process of claim 4.

11. A composition for use as a anti-fungal agent comprising the culture produced by the process of claim 5.

12. A composition for use as a anti-fungal agent comprising the culture produced by the process of claim 6.

13. The composition as described in claim 7 further comprising a sticking agent.

14. The composition as described in claim 11 further comprising a sticking agent.

15. The composition as described in claim 12 further comprising a sticking agent.

16. The composition as described in claim 7 further comprising a second fungicide different from said fungicidal steroid inhibitor.

17. The composition as described in claim 16 wherein said second fungicide is selected from the group consisting of carboxin, pentachloronitrobenzene, metalaxyl and mixtures thereof.

18. A method for controlling plant disease comprising applying a fungicidal or fungi inhibiting amount of the composition of claim 7 to the locus of a plant, seedling or seed.

19. The method as described in claim 18 wherein said step of applying comprises applying said composition onto a seed.

20. The method as described in claim 19 wherein said seed is selected from the group consisting of cottonseeds, soybeans, beans, citrus seeds, apple seeds, and seeds of zinnia.

21. A composition for use as a anti-fungal agent comprising *Gliocladium virens* in combination with an amount of a fungicidal steroid inhibitor effective for inhibiting production of viridiol by said Gliocladium, without substantially inhibiting growth of said Gliocladium.

22. The composition as described in claim 21 wherein said steroid inhibitor is selected from the group consisting of triazoles, silanes and mixtures thereof.

23. The composition as described in claim 22 wherein said steroid inhibitor is selected from the group consisting of propiconazole, flusilazole, triadimenol and myclobutanil.

24. The composition as described in claim 21 wherein the amount of said steroid inhibitor is between about 0.5 to 1 ppm.

25. The composition as described in claim 21 further comprising a sticking agent.

26. The composition as described in claim 21 further comprising a second fungicide selected from the group consisting of carboxin, pentachloronitrobenzene, metalaxyl and mixtures thereof.

27. A method for controlling plant disease comprising applying a fungicidal or fungi inhibiting amount of the composition of claim 21 to the locus of a plant, seedling or seed.

28. The method as described in claim 27 wherein said step of applying comprises applying said composition onto a seed.

29. The method as described in claim 28 wherein said seed is selected from the group consisting of cottonseeds, soybeans, beans, citrus seeds, apple seeds, and seeds of zinnia.

* * * * *